US00PP14585P29

(12) United States Plant Patent
Klemm

(10) Patent No.: US PP14,585 P2
(45) Date of Patent: Mar. 9, 2004

(54) POINSETTIA PLANT NAMED 'NPCW02042'

(50) Latin Name: *Euphorbia pulcherrima*
Varietal Denomination: NPCW02042

(75) Inventor: Nils Klemm, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 10/452,073

(22) Filed: Jun. 2, 2003

(51) Int. Cl.[7] ..... A01H 5/00
(52) U.S. Cl. ..... Plt./307
(58) Field of Search ..... Plt./307

*Primary Examiner*—Kent Bell
(74) *Attorney, Agent, or Firm*—C. A. Whealy

(57) ABSTRACT

A new and distinct cultivar of Poinsettia plant named 'NPCW02042', characterized by its uniform and upright plant habit; dark green-colored leaves; dark red-colored flower bracts that resist fading; early flowering habit; and good post-production longevity.

1 Drawing Sheet

Botanical classification/cultivar denomination: *Euphorbia pulcherrima* Willd. cultivar NPCW02042.

BACKGROUND OF THE INVENTION

The present Invention relates to a new and distinct cultivar of Poinsettia plant, botanically known as *Euphorbia pulcherrima* Willd., and hereinafter referred to by the cultivar name 'NPCW02042'.

The new Poinsettia is a product of a planned breeding program conducted by the Inventor in Stuttgart, Germany. The objective of the breeding program is to create new freely branching Poinsettia cultivars with upright and uniform plant habit and attractive flower bract coloration.

The new Poinsettia originated from a cross-pollination made by the Inventor in 1997 of a proprietary selection of *Euphorbia pulcherrima* Willd. identified as code number P 466, not patented, as the female, or seed, parent, with a proprietary selection of *Euphorbia pulcherrima* Willd. identified as code number S 219, not patented, as the male, or pollen, parent. The cultivar NPCW02042 was discovered and selected by the Inventor in 1999 as a flowering plant within the progeny of the stated cross-pollination in a controlled environment in Stuttgart, Germany. The selection of this plant was based on its attractive leaf and flower bract coloration and uniform plant habit.

Asexual reproduction of the new Poinsettia by vegetative terminal cuttings taken in a controlled environment in Stuttgart, Germany since 2000, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'NPCW02042'. These characteristics in combination distinguish 'NPCW02042' as a new and distinct Poinsettia cultivar:

1. Upright and uniform plant habit.
2. Dark green-colored leaves.
3. Dark red-colored flower bracts that resist fading.

4. Early flowering; response time, about 7.5 weeks.
5. Good post-production longevity.

Plants of the new Poinsettia differ from plants of the parent selections primarily in plant habit and flower bract coloration.

Plants of the new Poinsettia can be compared to plants of the cultivar 490, disclosed in U.S. Plant Pat. No. 7,825. In side-by-side comparisons conducted in Stuttgart, Germany, plants of the new Poinsettia differed from plants of the cultivar 490 in the following characteristics:

1. Plants of the new Poinsettia flowered about five days later than plants of the cultivar 490.
2. Flower bract color of plants of the new Poinsettia was darker red than flower bract color of plants of the cultivar 490.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a single flowering plant of 'NPCW02042' grown in a container.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype.

The aforementioned photograph, following observations and measurements describe plants grown in Stuttgart, Germany under commercial practice in a glass-covered greenhouse with day temperatures ranging from 20 to 30° C., night temperatures ranging from 16 to 20° C., and a maximum light level of about 70 kilolux. Cuttings were harvested in August and planted into 12-cm containers when rooted and pinched once. Plants were flowered under natural season short day/long night conditions. Plants were about 15 weeks from unrooted cuttings when the photograph and the detailed botanical description were taken. In the following description, color references are made to The Royal Horticultural Society Colour Chart, 1995 Edition, except where general terms of ordinary dictionary significance are used.

Botanical classification: *Euphorbia pulcherrima* Willd. cultivar NPCW02042.

Parentage:

*Female, or seed, parent.*—Proprietary selection of *Euphorbia pulcherrima* Willd. identified as code number P 466, not patented.

*Male, or pollen, parent.*—Proprietary selection of *Euphorbia pulcherrima* Willd. identified as code number S 219, not patented.

Propagation:

*Type cutting.*—Vegetative terminal cuttings.

*Time to initiate roots.*—Summer: About 12 days at 22° C. Winter: About 15 days at 22° C.

*Time to produce a rooted cutting.*—Summer: About 20 days at 22° C. Winter: About 23 days at 22° C.

*Root description.*—Fibrous; freely-branching; white in color.

Plant description:

*Growth habit.*—Upright and uniform plant habit; inverted triangle; top of plant rounded; moderately vigorous.

*Plant height.*—About 25 to 30 cm.

*Plant diameter or spread.*—About 30 to 35 cm.

*Lateral branch description.*—Quantity per plant: About four to seven lateral branches develop after pinching. Length: About 25 cm. Diameter: About 5 to 10 mm. Internode length: About 1 to 4 cm. Texture: Smooth, glabrous. Color: 143A overlain with 183A.

*Foliage description.*—Arrangement: Alternate, single. Quantity of leaves: About 8 to 15 per lateral branch. Length: About 4 to 12 cm. Width: About 3 to 7 cm. Shape: Ovate. Apex: Acute. Base: Obtuse. Margin: Entire with slight irregular lobing. Venation pattern: Pinnate. Texture, upper and lower surfaces: Glabrous, smooth. Color: Developing foliage, upper surface: 144B. Developing foliage, lower surface: 143C. Fully expanded foliage, upper surface: 139A. Fully expanded foliage, lower surface: 137B. Venation, upper surface: 139A. Venation, lower surface: 181A. Petiole: Length: About 2 to 4 cm. Diameter: About 2 to 3 mm. Texture: Glabrous, smooth. Color, upper and lower surfaces: 183A.

Inflorescence description:

*Inflorescence type and habit.*—Inflorescences are compound corymbs of cyathia with colored flower bracts subtending the cyathia. Inflorescences not persistent.

*Fragrance.*—None detected.

*Natural flowering season.*—Autumn/winter; flower initiation and development is induced under short day/long night conditions.

*Response time.*—Early flowering, about 7.5 weeks.

*Post-production longevity.*—Plants of the new Poinsettia maintain good substance and bract color for about three to four weeks under interior conditions and about four to five weeks under greenhouse conditions.

*Quantity of inflorescences.*—One per lateral branch; about four to seven per plant.

*Inflorescence size.*—Diameter: About 15 to 20 cm. Height (depth): About 2 to 5 cm.

*Flower bracts.*—Quantity of fully developed flower bracts: About six to eight per inflorescence. Length: About 7 to 10 cm. Width: About 5 to 7 cm. Shape: Ovate. Apex: Acute. Base: Obtuse. Margin: Entire with occasional lobing. Texture, upper and lower surfaces: Glabrous, smooth. Surface: Flat. Color: Developing and fully expanded bracts, upper surface: 45A; color does not fade with development. Developing and fully expanded bracts, lower surface: 53B. Venation, upper and lower surfaces: Same as lamina. Bract petiole: Length: About 1 to 3 cm. Diameter: About 2 mm. Texture: Glabrous, smooth. Color, upper and lower surfaces: 183B.

*Cyathia.*—Quantity of cyathia: About four to six per corymb. Diameter of cyathia cluster: About 1.5 to 2.5 cm. Length: About 4 to 7 mm. Diameter: About 3 to 5 mm. Shape: Ovoid. Color, immature and mature: 143C.

*Nectaries.*—Quantity of nectaries: One per cyathium. Diameter: About 2 to 3 mm. Color: 13A to 14B.

*Peduncle.*—Length: About 1 to 2 mm. Diameter: About 1 mm. Aspect: Erect. Strength: Moderately strong. Texture: Glabrous, smooth. Color: 144C.

*Reproductive organs.*—Stamens: Quantity of stamens: About five to ten per cyathium. Anther shape: Ovoid. Anther length: About 1 mm. Anther color: 9A to 12A. Amount of pollen: Moderate. Pollen color: 9A to 12A. Pistils: Quantity of pistils: One per cyathium. Pistil length: About 3 to 5 mm. Style length: About 2 to 3 mm. Stigma color: 185A.

Disease/pest resistance: Resistance to pathogens and pests common to Poinsettias has not been observed on plants grown under commercial conditions.

Temperature tolerance: Plants of the new Poinsettia have been observed to tolerate temperatures from 14 to 38° C.

It is claimed:

1. A new and distinct cultivar of Poinsettia plant named 'NPCW02042', as illustrated and described.

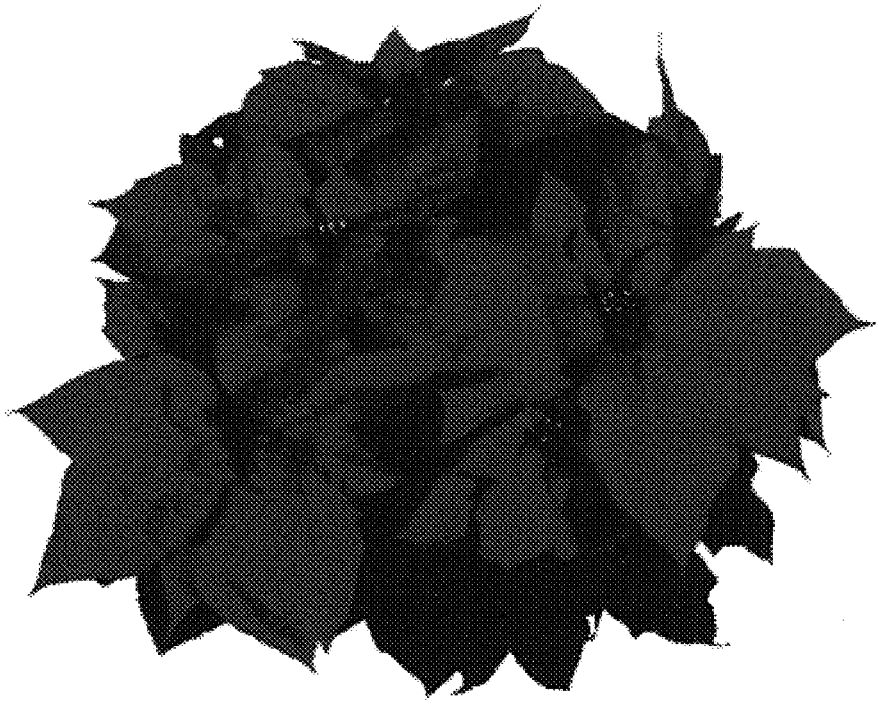

* * * * *